United States Patent [19]

Witt

[11] Patent Number: 4,902,621

[45] Date of Patent: Feb. 20, 1990

[54] TEST REAGENT FOR AMYLASE DETERMINATION

[75] Inventor: Peter Witt, Neuenburg, Fed. Rep. of Germany

[73] Assignee: Akzo N.V., Arnhem, Netherlands

[21] Appl. No.: 93,936

[22] Filed: Sep. 8, 1987

[30] Foreign Application Priority Data

Sep. 10, 1986 [EP] European Pat. Off. ....... 86.201556.7

[51] Int. Cl.$^4$ .............................................. C12N 9/96
[52] U.S. Cl. ...................................... 435/188; 435/22; 435/201; 435/202; 435/203; 435/204; 435/205
[58] Field of Search ................... 435/22, 188, 201–205

[56] References Cited

U.S. PATENT DOCUMENTS 4,259,440  3/1981  Gupta et al. ........................... 435/19
4,649,108  3/1987  Blair ..................................... 435/22

Primary Examiner—Robert A. Wax
Attorney, Agent, or Firm—William M. Blackstone

[57] ABSTRACT

An aqueous stabilized enzyme preparation to be used for measuring the amount of α-amylase in a liquid sample like serum or urine containing a blocked and labeled oligosaccharide being the substrate for the α-amylase to be measured in the presence of exo-enzymes which aqueous preparation, preferably consisting of two separate solutions is stabilized by adding a buffer, a taurocholic acid derivative, an albumin, and a polyhydric alcohol.

9 Claims, No Drawings

TEST REAGENT FOR AMYLASE DETERMINATION

The invention relates to an aqueous stabilized enzyme preparation to be used for measuring the amount of α-amylase in a liquid sample.

The measurement of α-amylase in biological fluids, especially in urine and serum, is very important clinically in the diagnosis of pancreatic disorders.

A number of assays are known employing oligosaccharides containing at least 3 glucose units which reducing-end glucose unit is coupled to a label cleavable by a glucosidase which label exhibits a measurable change upon cleavage, and which terminal glucose unit is blocked inhibiting cleavage by exo-enzymes.

The label which is bonded by an α- or β-linkage to the reducing-end glucose unit can be a chromophore like p-, or o-nitrophenol, a fluorophore like a coumarin derivative, or a chemi- or bioluminescent substituent, e.g. luciferin.

Blocking of the terminal glucose unit can be performed by periodate oxidation, or by introducing blocking substituents like acetals, ketals, or any other blocking group known per se.

The oligosaccharide being the substrate for α-amylase to be measured has at least three glucose units, and preferably six to eight glucose units.

Measurement of α-amylase in a liquid sample, e.g. urine or serum, takes place by contacting said sample with the above described oligosaccharide substrate in the presence of two exo-enzymes, being α-, and/or β-glucosidase and glucoamylase.

In the absence of α-amylase the blocking group prevents exo-enzymes from breaking down the substrate so that no measurable change occurs.

However, if α-amylase is present in the sample to be tested this endo-enzyme will cleave the oligosaccharide substrate into smaller fragments which can be acted on by the above exo-enzymes, which causes the release of the label, e.g. the chromophore, which release can be measured.

The known reagents, being substrate, exo-enzymes and additional ingredients, are always in a lyophilized form.

There is a long-felt need to supply such reagents in the form of aqueous solutions but, unfortunately, the stability of aqueous solutions of the known reagents is rather small.

We found that the stability of the known lyophilized reagents, dissolved in water, amounts from two to twenty days at a temperature of 4° C., which period is too short to make such aqueous test reagents suited for marketing.

The present invention relates to the preparation of an aqueous stabilized enzyme preparation to be used for measuring the amount of α-amylase in a liquid sample comprising:
a. an oligosaccharide substrate for α-amylase containing at least three glucose units which reducing-end glucose unit is coupled to a label cleavable by α-, or β-glucosidase which label exhibits a measurable change upon cleavage, and its terminal glucose unit is blocked inhibiting cleavage by exo-enzymes,
b. two exo-enzymes being glucoamylase and α-, or β-glucosidase,
c. as stabilising agent a composition consisting of:
1. a buffer,
2. a water-soluble metal salt of taurocholic acid,
3. albumin, and
4. a polyhydric alcohol.

The buffer in the stabilising composition can be a PIPES-buffer, at a concentration of 1.5–6.0 mmol/liter, but a phosphate buffer is preferred.

The taurocholic acid derivative is preferably an alkali metal salt of taurocholic acid, e.g. sodium taurocholate, at a concentration of 0.3–1.5 mmol/liter.

Albumin is preferably bovine albumin, at a concentration of 0.5–4.0 g/liter.

The polyhydric alcohol can be any poly alcohol but preferably glycerol is used at a concentration of 40–200 mmol/liter.

Other ingredients may be added to the aforesaid aqueous solution, like a preservative agent, e.g. sodium azide, or an enzyme activator, e.g. an alkali metal chloride.

It is preferable to provide the test reagent according to the present invention in two separate aqueous solutions which are brought together before the determination of α-amylase takes place. In this form the test reagent consists of:
solution A comprising the blocked and labeled oligosaccharide substrate in a buffered aqueous solution, and
solution B comprising the exo-enzymes in a buffered aqueous solution to which is added as stabilizing agents a composition consisting of:
1. a water-soluble metal salt of taurocholic acid, preferably an alkali metal taurocholate at a concentration of 0.3–1.5 mmol/liter.
2. albumin, preferably bovine albumin at a concentration of 0.5–4.0 g/liter, and
a polyhydric alcohol, preferably glycerol, at a concentration of 40–200 mmol/liter.

The aqueous stabilised test reagent according to the present invention is far superior to the known test reagents.

Where the stability of the latter freeze dried reagent, dissolved in water, have a stability of less than seven days at an average at a temperature of 4° C., the stability of the present aqueous test reagent is at least two to three years at a temperature of 4° C.

Another surprising advantage is that the increasing of the absorption of the reagent blank is up to two times smaller if the final reagent includes a water-soluble metal salt of taurocholic acid, albumin, and a polyhydric alcohol than those of the same reagent without these substances.

A further advantage is that the present test reagents require a substantial shorter incubation time than the known reagents.

DETAILED EXAMPLES

I. Test reagent (one solution)

0.395 mmol/l p-Nitrophenyl-α-D-maltoheptaoside-blocked
6.650 U/l α-glucosidase
2.700 U/l glucoamylase
66.7 mmol/l phosphate buffer
0.745 mmol/l sodium taurocholate
7.69 mmol/l sodium azide
1.00 g/l bovine albumin
87 mmol/l glycerol
pH 7.1.

II. Test reagent (two solutions)

solution A
0.79 mmol/l p-Nitrophenyl-α-D-maltoheptaoside-blocked
66.7 mmol/l phosphate buffer
7.69 mmol/l sodium azide.
34 mmol/l sodium chloride solution B
13.500 U/l α-glucosidase
5.400 U/l glucoamylase
1.3 mmol/l phosphate buffer
7.69 mmol/l sodium azide
1.49 mmol/l sodium taurocholate
2.0 g/l bovine albumin
174 mmol/l glycerol Test Assay 1000 μl test reagent were added to 50 μl serum, followed by incubation at 25°, 30° and 37° C. respectively during two minutes. The change in absorbance at 405 nm per minute was determined according to the following calculation: U/l
α-amylase=factor×$\Delta E_{405\ nm}$/min.

I claim:

1. An aqueous stabilized enzyme preparation to be used for measuring the amount of α-amylase in a liquid sample comprising:
   (a). an oligosaccharide substrate for α-amylase comprising at least three glucose units, wherein the reducing-end glucose unit is coupled to a label cleavable by α- or β-glucosidase, said label being one that exhibits a measurable change upon cleavage, and wherein the terminal glucose unit is blocked to inhibit cleavage by exo-enzymes,
   (b). at least two exo-enzymes being glucoamylase and at least one glucosidase selected from the group consisting of α- and β-glucosidase, and
   (c). a stabilizing agent composition comprising:
   a buffer,
   a water-soluble metal salt of taurocholic acid,
   albumin and
   a polyhydric alcohol.

2. The aqueous stabilized enzyme preparation according to claim 1 consisting of two separate aqueous solutions that are brought together before measuring α-amylase, the first solution comprising the blocked and labeled oligosaccharide substrate in a buffered aqueous solution and the second solution consisting of a buffered aqueous solution comprising the exo-enzymes and a stabilizing agent, wherein said stabilizing agent comprises:
   a water-soluble metal salt of taurocholic acid,
   albumin and a polyhydric alcohol.

3. The enzyme preparation according to claim 1, wherein the buffer is a phosphate-buffer, the taurocholic acid derivative is an alkali metal salt of taurocholic acid, albumin is bovine albumin and the polyhydric alcohol is glycerol.

4. The enzyme preparation according to claim 2, wherein the taurocholic acid salt is an alkali metal taurocholate.

5. The enzyme preparation according to claim 4, wherein the alkali metal taurocholate is present in the second solution at a concentration of about 0.3 to about 1.5 mmol/liter.

6. The enzyme preparation according to claim 2, wherein the albumin is bovine albumin.

7. The enzyme preparation according to claim 6, wherein the bovine albumin is present in the second solution at a concentration of about 0.5 to about 4.0 g/liter.

8. The enzyme preparation according to claim 2, wherein the polyhydric alcohol is glycerol.

9. The enzyme preparation according to claim 8, wherein the glycerol is present in the second solution at a concentration of about 40 to about 200 mmol/liter.

* * * * *